United States Patent [19]

Kennedy et al.

[11] Patent Number: 5,575,757
[45] Date of Patent: Nov. 19, 1996

[54] ENDOSCOPE WITH FOCUSING MECHANISM

[75] Inventors: John E. Kennedy, Lowell, Mass.; Paul V. Lucey, Sandown, N.H.; Yury E. Kazakevich, Methuen; Gheorghe Mihalca, Chelmsford, both of Mass.; Gary D. Henley, Yukon; Clifford A. Dowdy, Piedmont, both of Okla.

[73] Assignee: Smith & Nephew Endoscopy Inc., Andover, Mass.

[21] Appl. No.: 958,688

[22] Filed: Oct. 9, 1992

[51] Int. Cl.$^6$ ............................................. A61B 1/00
[52] U.S. Cl. ........................... 600/167; 600/109; 348/65; 359/700
[58] Field of Search ............................. 128/4,6; 348/65, 348/68, 71; 385/117; 359/383, 384, 406, 422, 425, 426, 699, 700, 704, 826; 600/167, 163; 403/348, 355, 359, 377

[56] References Cited

U.S. PATENT DOCUMENTS

| | | | |
|---|---|---|---|
| Re. 33,854 | 8/1992 | Adair | 600/122 |
| 2,317,875 | 4/1943 | Athey et al. | 88/16.6 |
| 4,074,306 | 2/1978 | Kakinuma et al. | 358/1 |
| 4,300,812 | 11/1981 | Nakahashi | 350/42 |
| 4,488,039 | 12/1984 | Sato et al. | 250/216 |
| 4,491,865 | 1/1985 | Danna et al. | 358/98 |
| 4,515,037 | 5/1985 | Block | 403/348 X |
| 4,532,918 | 8/1985 | Wheeler . | |
| 4,593,313 | 6/1986 | Nagasaki et al. | 350/445 |
| 4,598,980 | 7/1986 | Doi et al. | 350/445 |
| 4,600,940 | 7/1986 | Sluyter . | |
| 4,639,772 | 1/1987 | Sluyter et al. | 358/98 |
| 4,641,635 | 2/1987 | Yabe . | |
| 4,643,170 | 2/1987 | Miyazaki et al. . | |
| 4,662,584 | 11/1986 | Nagasaki et al. | 358/98 |
| 4,677,471 | 6/1987 | Takamura et al. | 358/98 |
| 4,699,125 | 10/1987 | Komatsu . | |
| 4,712,133 | 12/1987 | Kikuchi | 358/98 |
| 4,720,178 | 1/1988 | Nishioka et al. | 350/401 |
| 4,728,216 | 3/1988 | Disborg | 403/359 X |
| 4,736,734 | 4/1988 | Matsuura et al. . | |
| 4,745,470 | 5/1988 | Yabe et al. | 358/98 |
| 4,745,471 | 5/1988 | Takamura et al. | 358/98 |
| 4,746,975 | 5/1988 | Ogiu | 358/98 |
| 4,777,524 | 10/1988 | Nakajima et al. | 358/98 |
| 4,779,130 | 10/1988 | Yabe | 358/98 |
| 4,780,762 | 10/1988 | Nagasaki | 358/166 |
| 4,791,480 | 12/1988 | Muranaka | 358/98 |
| 4,821,116 | 4/1989 | Nagasaki et al. | 358/98 |
| 4,831,437 | 5/1989 | Nishioka et al. | 358/98 |
| 4,841,363 | 6/1989 | Ams et al. | 358/98 |
| 4,844,071 | 7/1989 | Chen et al. . | |
| 4,845,553 | 7/1989 | Konomura et al. | 358/98 |
| 4,845,555 | 7/1989 | Yabe et al. | 358/98 |
| 4,846,155 | 7/1989 | Kimura . | |

(List continued on next page.)

FOREIGN PATENT DOCUMENTS

| | | |
|---|---|---|
| 0496142A1 | 7/1992 | European Pat. Off. . |
| 57-72134 | 10/1980 | Japan . |
| 2168216 | 6/1990 | Japan . |
| 1125783 | 11/1979 | U.S.S.R. . |
| 1401003 | 7/1975 | United Kingdom . |
| 2070715 | 9/1981 | United Kingdom ................... 128/4 |
| WO93/25138 | 12/1993 | WIPO . |
| WO93/25137 | 12/1993 | WIPO . |

*Primary Examiner*—Richard J. Apley
*Assistant Examiner*—John Mulcahy
*Attorney, Agent, or Firm*—Fish & Richardson P.C.

[57] ABSTRACT

An endoscope includes a focusing mechanism having a focus control element at a proximal end of the endoscope and a mechanical coupling connecting the focus control element to an image transmitting device (e.g., an electro-optical sensor or one or more optical fibres) mounted at a distal end of an elongated insertion section of the endoscope. Rotation of the focus control element moves the image transmitting device with respect to a lens assembly of the endoscope to focus the image received by the lens assembly. The focus control element may be disengaged from the mechanical coupling by pulling it axially along the length of the insertion section whereby the focusing mechanism may be easily disassembled.

16 Claims, 8 Drawing Sheets

U.S. PATENT DOCUMENTS

| | | | |
|---|---|---|---|
| 4,853,772 | 8/1989 | Kikuchi | 358/98 |
| 4,858,002 | 8/1989 | Zobel | 358/98 |
| 4,866,526 | 9/1989 | Ams et al. | 358/98 |
| 4,867,137 | 9/1989 | Takahashi . | |
| 4,868,646 | 9/1989 | Tsuji | 358/98 |
| 4,870,487 | 9/1989 | Noguchi et al. | 358/98 |
| 4,879,992 | 11/1989 | Nishigaki et al. . | |
| 4,882,623 | 11/1989 | Uchikubo . | |
| 4,884,133 | 11/1989 | Kanno et al. | 358/98 |
| 4,884,134 | 11/1989 | Tsuji et al. | 358/98 |
| 4,891,697 | 1/1990 | Saito et al. | 358/98 |
| 4,894,715 | 1/1990 | Uchikubo et al. | 358/98 |
| 4,905,668 | 3/1990 | Ohsawa . | |
| 4,916,534 | 4/1990 | Takahashi et al. | 358/98 |
| 4,918,521 | 4/1990 | Yabe et al. | 358/98 |
| 4,928,172 | 5/1990 | Uehara et al. | 358/98 |
| 4,963,960 | 10/1990 | Takami | 358/98 |
| 4,967,269 | 10/1990 | Sasagawa et al. | 358/98 |
| 4,969,450 | 11/1990 | Chinnock et al. | 600/163 X |
| 4,989,586 | 2/1991 | Furukawa . | |
| 5,010,876 | 4/1991 | Henley et al. . | |
| 5,049,989 | 9/1991 | Tsuji | 358/98 |
| 5,050,584 | 9/1991 | Matsuura . | |
| 5,056,503 | 10/1991 | Nagasaki et al. . | |
| 5,056,902 | 10/1991 | Chinnock et al. | 600/163 X |
| 5,222,477 | 6/1993 | Lia . | |

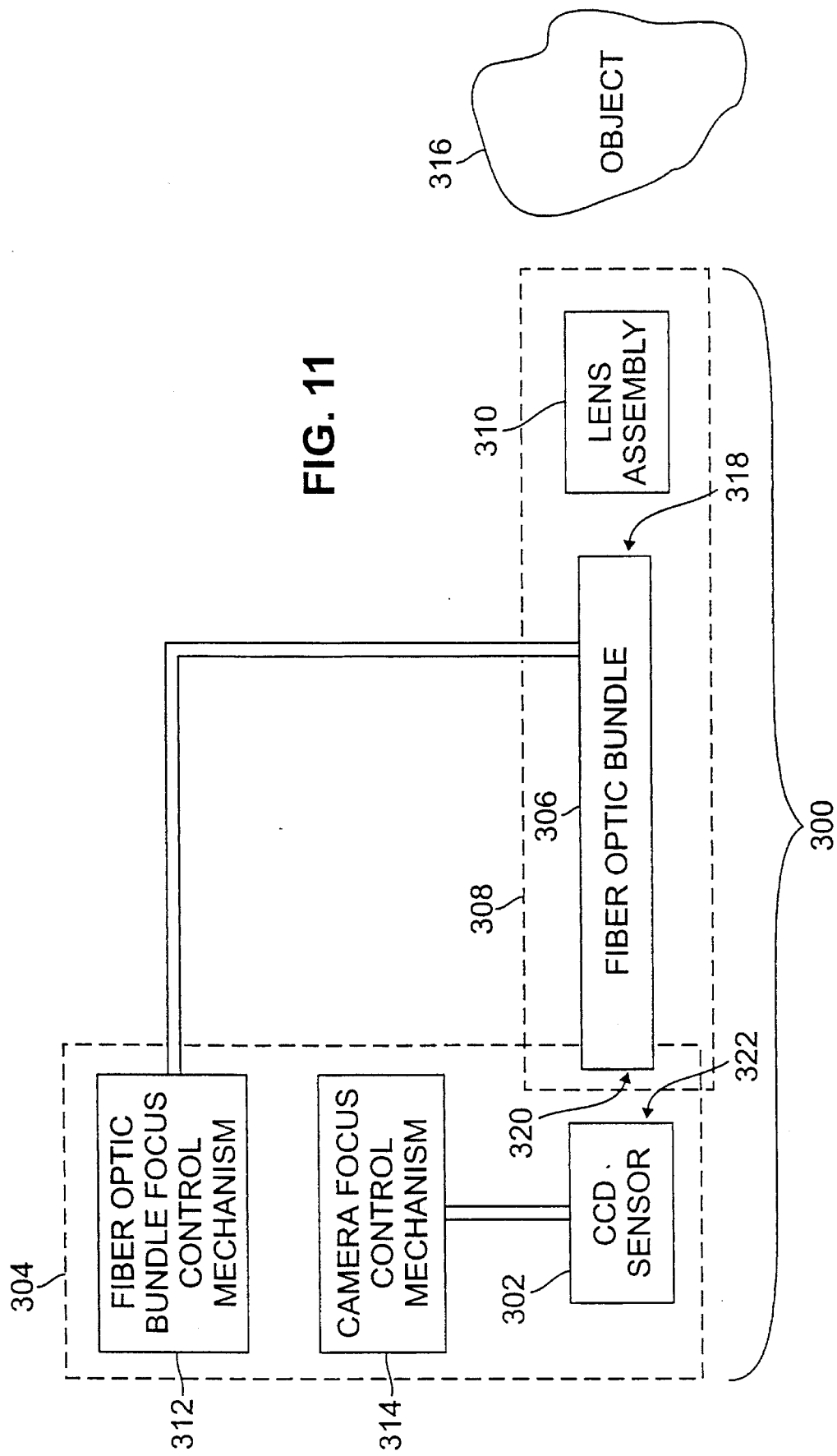

ENDOSCOPE WITH FOCUSING MECHANISM

BACKGROUND OF THE INVENTION

This invention relates to endoscopes and more particularly to electronic endoscopes.

Generally, endoscopes are instruments for visualizing the interior of an object, such as the human body (e.g., an internal organ or anatomical body passage). A typical endoscope includes an elongated flexible or rigid outer tube within which a lens system is disposed at a distal end. The image of the object being viewed by the optical system is transmitted through an optical system from the distal end to a proximal end of the tube for viewing by the user or for reception by a camera. Some endoscopes also carry fiber optic cables for illuminating the area of observation with light supplied by an external source.

In some endoscopes, the optical system includes a bundle of fibre optic cables positioned immediately proximally of a stationary objective lens assembly located at the distal end of the tube. The lens assembly focuses the image into the end of the fibre bundle, which in turn transmits the image proximally.

An electronic endoscope typically includes an electro-optic image sensor (such as a charge coupled device or CCD) in place of the fibre optic bundle. The CCD is positioned closely adjacent the objective lens assembly and generates a video signal of the object being observed. The video signal is transmitted by an electrical cable to the proximal end of the endoscope and is processed for viewing on a display such as a CRT monitor.

SUMMARY OF THE INVENTION

This invention provides an endoscope with a focusing mechanism having a focus control element at a proximal end of the endoscope and a mechanical coupling connecting the focus control element to an image transmitting device mounted at the distal end of an elongated insertion section of the endoscope for causing the image transmitting device to move along the length of the insertion section in response to activation of the focus control element. In one general aspect of this concept, the image transmitting device includes electro-optical sensor. In another aspect, the image transmitting devices comprises one or more optical fibres.

Embodiments of the invention include the following features. The focus control element is a rotatable manipulator accessible to a user. The mechanical coupling is a rigid actuator coupled between the manipulator and the sensor, with the actuator moving along the length of the insertion section in response to rotation of the manipulator. This arrangement allows an image viewed by the endoscope to be easily focused while in use without removal from the surgical site.

In one embodiment, the mechanical coupling includes a helical surface disposed on an inner sleeve which surrounds and is rotatable around the insertion section. The rigid actuator includes a follower configured to engage the helical surface and to move along the helical surface in response to rotation of said rotatable manipulator. The rotatable manipulator has an outer sleeve which surrounds the inner sleeve, and the inner sleeve and the outer sleeve are connected by a coupling which may be selectively engaged and disengaged by relative motion of said inner and outer sleeves along the length of the insertion section. As a result, the focusing mechanism is easy to assemble and disassemble.

The outer sleeve of the rotatable manipulator rotates smoothly with little physical effort and can be operated easily with one hand. The mechanical coupling further includes a slot provided along and in parallel with a portion of the length of the insertion section, with the follower riding within said slot. The slot permits the rotatable manipulator to focus the image while maintaining a non-rotating image on an external display.

In another embodiment, the manipulator includes an element that is ferromagnetically coupled to the rigid actuator through an external wall of the insertion section. This avoids passing a mechanical element (such as follower discussed above) through the external wall, thereby allowing the interior of the insertion section to be more completely sealed to reduce the risk of foreign material coming into contact with the electrical and optical components of the device.

In another aspect of the invention, the electronic endoscope is disposable, and the insertion section is sterilized and packaged in a sterile container together with a sterilized conduit that is used to connect the insertion section to a control unit; the conduit carries an optical fiber for transmitting light from the control unit to the insertion section, and an electrical cable for carrying electrical signals from the sensor to the control unit.

The endoscope and integral cable for providing both electrical and illumination requirements to the endoscope has a single connector for connection to a video processor (camera control unit). The endoscope with integral cable is provided in a sterile container so that the endoscope is disposable after use in a surgical procedure.

Other features and advantages of the invention will become apparent from the following detailed description, and from the claims.

BRIEF DESCRIPTION OF THE DRAWINGS

FIG. 2a is an enlarged view of the region enclosed by 2a—2a of FIG. 2.

FIG. 11 is a schematic representation of another alternative embodiment of an endoscope according to the invention.

DESCRIPTION OF THE PREFERRED EMBODIMENTS

Figure 1:
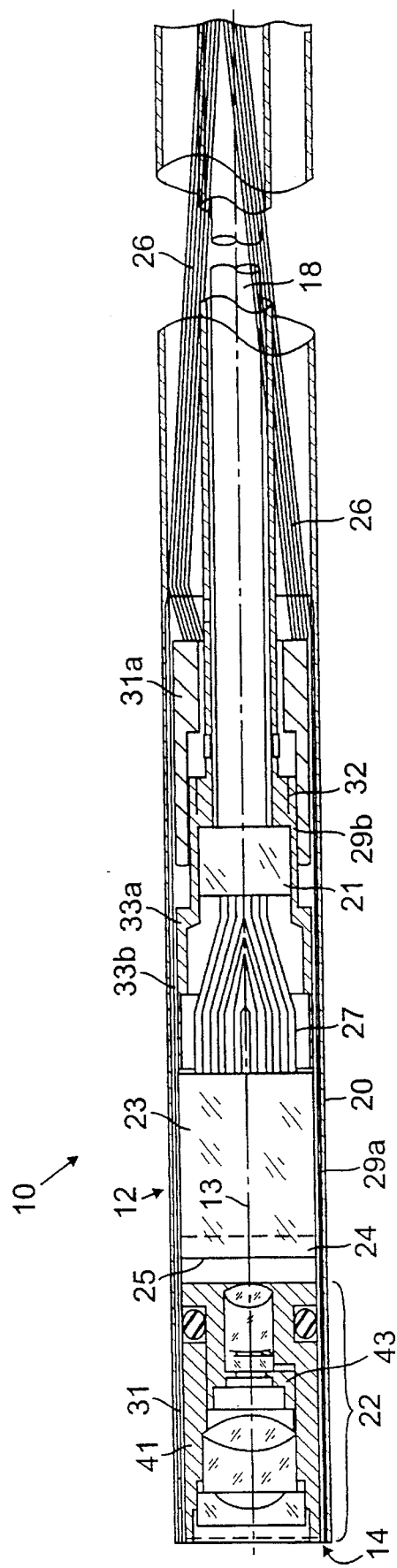
FIG. 1 is a cross-sectional side view of a distal region of an endoscope according to the invention.
Figure 2:
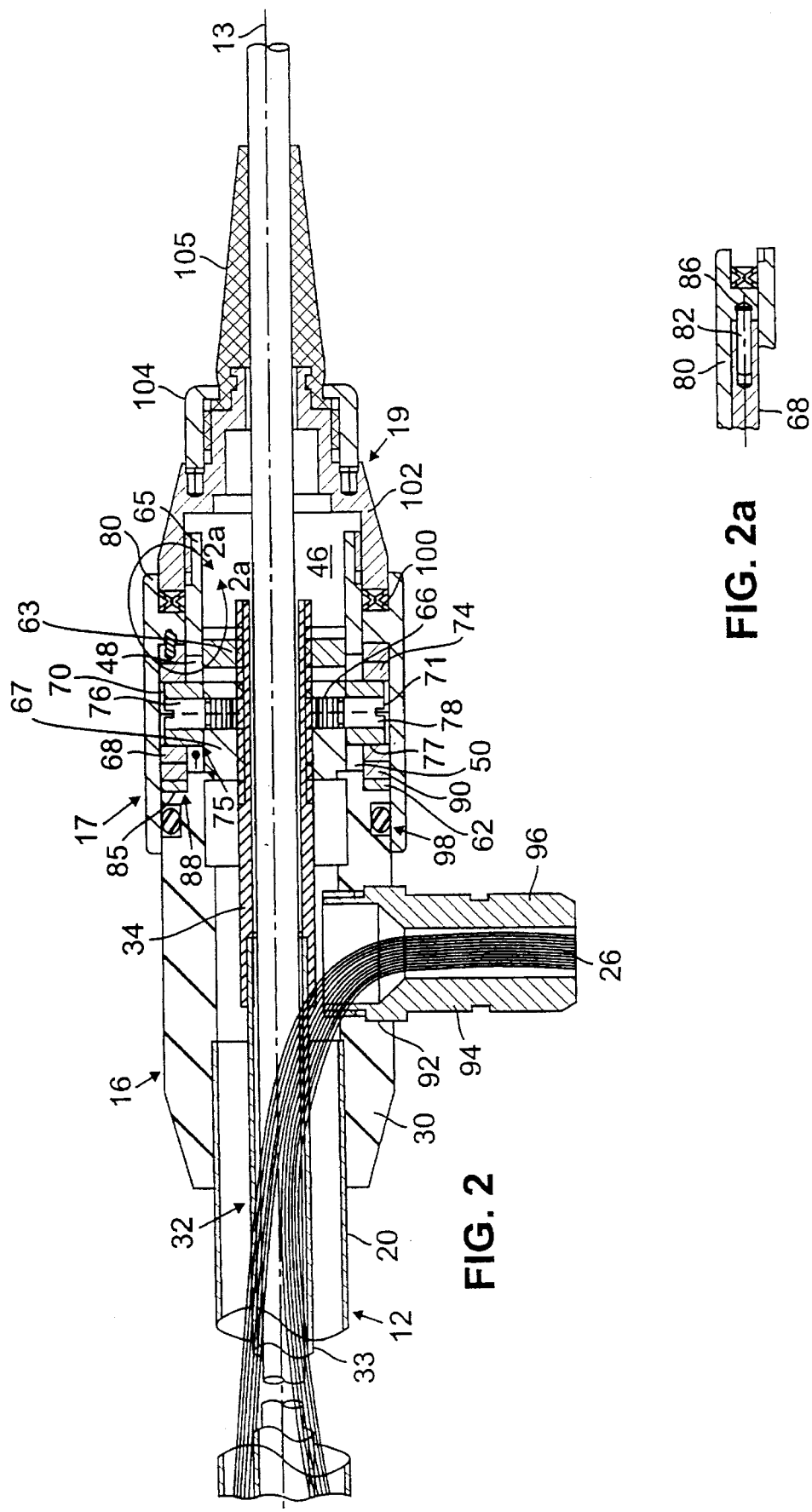
FIG. 2 is a cross-sectional side view of a proximal rear end portion of the endoscope of FIG. 1.
Figure 6:
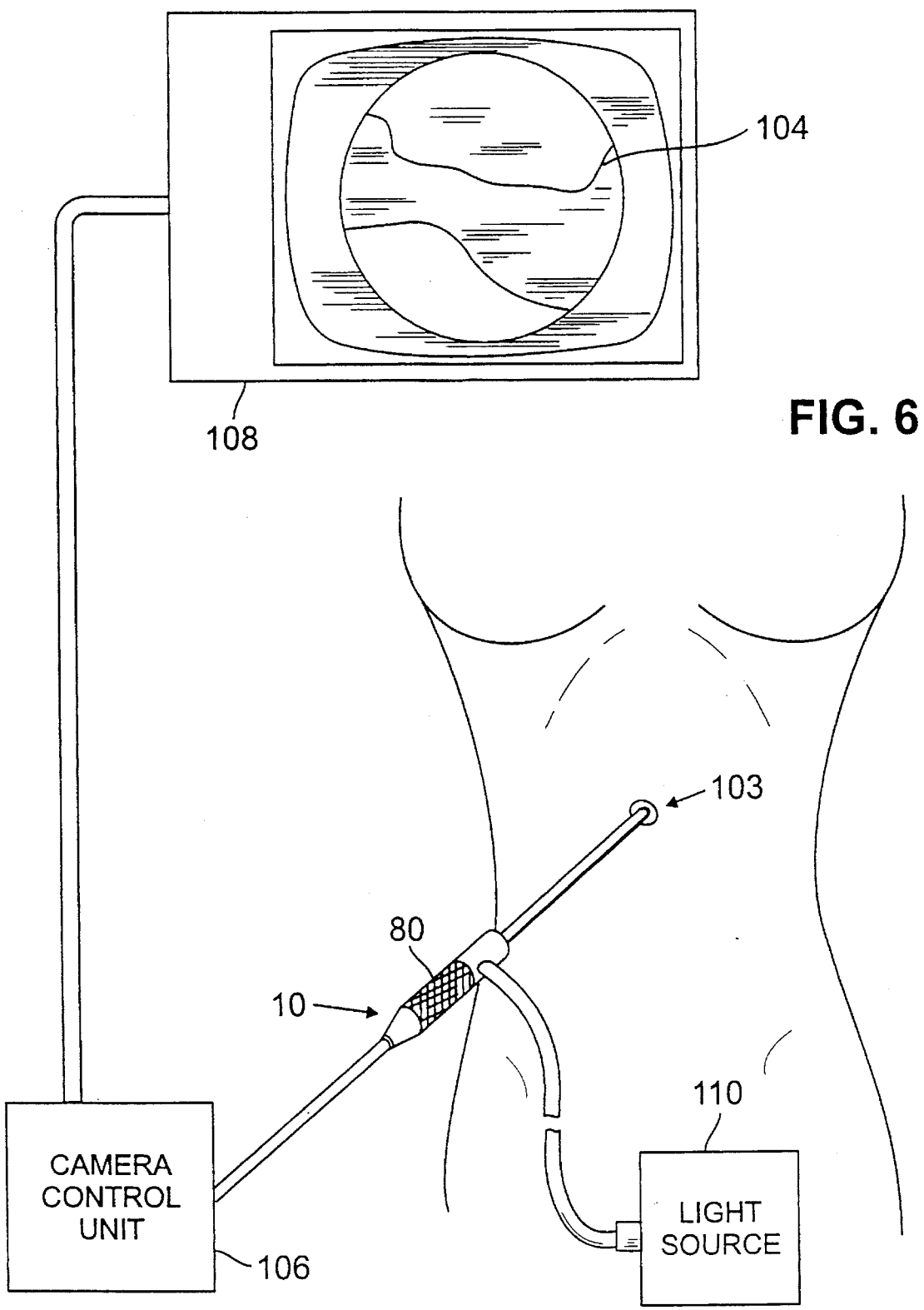
FIG. 6 is a diagrammatic view of the endoscope of FIG. 1 in use.

As shown in FIGS. 1 and 2, an electronic endoscope 10 includes an elongated insertion section 12 for insertion into a body cavity or narrow body passage 103 (See FIG. 6) to observe an object therein. Elongated insertion section 12 extends along a longitudinal axis 13 of endoscope 10 from a distal end 14 to a handle 16 at the proximal end 19 of endoscope 10. Handle 16 permits the user to position elongated insertion section 12 of endoscope 10 appropriately and also houses a focus control mechanism 17 for endoscope 10, which is described in detail below. A cable 18 extends from proximal end 19 for connection to a power source and camera control unit 106 (FIG. 6). Images observed at distal end 14 of endoscope 10 are processed by the video processor for viewing on a display unit, such as a color CRT 108.

Elongated insertion section 12 includes an outer tube 20 for housing an objective lens assembly 22, an image transmitting device (which in this embodiment includes an electro-optic module 23, having an electro-optical sensor 24 (e.g. a charge-coupled device (CCD)) for converting optical images of the received light into electrical image signals), and light guiding fiber optic elements 26 for illuminating the area being observed. Outer tube 20 extends from distal end 14 of endoscope 10 to a first end of a main housing 30 at handle 16 where tube 20 is soldered within a counterbore of main housing 30. Outer tube 20, fabricated from anodized aluminum, has a length of about 13 inches, an outer diameter of 0.379 inches and a wall thickness of approximately 0.010 inches.

Elongated insertion section 12 further includes an inner cylindrical tube 31 and a CCD tube 32, each coaxially disposed within outer tube 20. Inner cylindrical tube 31 extends proximally approximately 2.4 inches from the distal end 14 of the outer tube 20 to an enlarged proximal end 31a that receives the distal end of CCD tube 32. Tube 31 is radially spaced from outer tube 20 to provide a cylindrical passage within which fiber optic elements 26 pass to distal end 14. CCD tube 32 is shown having a first cylindrical member 33 extending from a region directly behind lens assembly 22 to a region partially within main housing 30 and a second extension member 34 soldered to first cylindrical member 33 which extends to focus control mechanism 17. The distal end 33a of CCD tube 32 has a pair of enlarged diameter regions 29a, 29b as shown to receive electro-optic module 23 and a crimped end of cable 18, respectively. Electro-optic module 23 is secured into region 29a of CCD tube 32 with epoxy. Cable 18 has a woven ground conductor surrounded by a band 21 which is crimped to prove a snug fit within region 29b.

Figure 3:
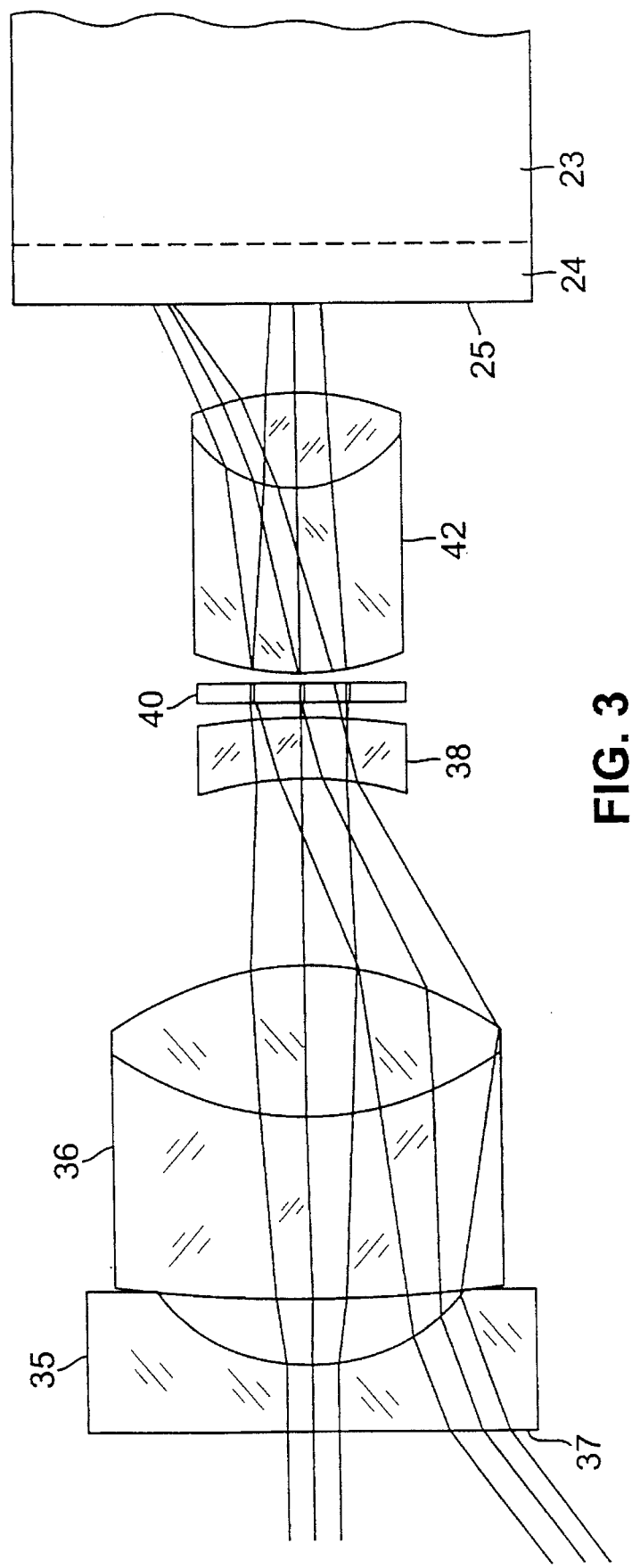
FIG. 3 is a diagrammatic view of a lens assembly of the endoscope of FIG. 1.

Referring also to FIG. 3, an optical image from the area being observed is provided to a front face 25 of CCD 24 by lens assembly 22 through a series of four lenses. Images incident on lens assembly 22 pass through a negative lens 35, a doublet lens 36, a meniscus lens 38, an aperture stop 40, and a second doublet 42, and are incident on face 25 of CCD 24. Negative lens 35 has a flat distal surface 37. Distal surface 37 being flat provides the advantage of being easily cleaned and maintained. Doublets 36 and 42 are fabricated from a pair of lens elements of glass materials having different optical characteristics (e.g. refractive index) that are joined with a thin layer of epoxy. Lens elements 35–42 are spaced from each other by air and are encased within a lens housing 41. Meniscus lens 38, aperture stop 40, and second doublet 42 are supported by a spacer 43 (FIG. 1) to assure their concentricity within lens housing 41. The four-lens objective lens assembly 22 supported within lens housing 41 has a physical length of about 16 mm, a focal length of 4 mm, and an f number of 5. Lens assembly 22 provides a field of view of approximately 75 degrees. Lens assembly 22 fits snugly within tube 31 and is recessed from the tip of outer tube 20 to protect exposed distal surface 37 of lens element 35. Lens assembly 22 and inner cylindrical tube 31 are rigidly attached with epoxy.

Electro-optic module 23 is the solid-state image sensor portion of a commercially available electronic camera (lens objective removed) which is manufactured by Panasonic Communications and Systems Company, Secaucus, N.J., model No. GP-KS202. Electro-optic module 23 is sized to fit within distal end 33b of CCD tube 32, and includes a CCD 24 with its associated preamplifier/driver circuitry (not shown). Images generated by CCD 24 are transferred via the preamplifier/driver circuit (not shown) to individual wires 27 of cable 18. Cable 18 is inserted within CCD tube 32 and supplies power to electro-optic module 23 and receives electrical image signals to be provided to video processor 106 or camera control unit external to endoscope 10 via wires 27.

Fiber optic elements 26 are disposed in a cylindrical region between outer surfaces of both inner cylindrical tube 31 and CCD tube 32 and the inner surface of outer tube 20 along the length of insertion section 12 extending from distal end 14 to main housing 30 such that in operation, a ring of light is provided around the area viewed by lens assembly 22. During assembly, fiber optic elements 26 are fed in an evenly spaced manner within the region between tubes 20 and 31 (before inner cylindrical tube 31 is glued in place). The loose ends of fiber optic elements 26 are allowed to extend beyond the distal end 14. Fiber optic elements 26 are potted in place with an epoxy and portions extending beyond distal end 14 are then cut and polished to ensure a clear epoxy-free glass surface at the ends of each fiber optic element. Fiber optic elements 26 are fabricated using a highly transmissive glass-like material, manufactured by Cuda Products Corp., Jacksonville, Fla., such that light provided from an external light source 110 (See FIG. 6) to the proximal end of fiber optic elements 26 is provided to distal end 14 with minimal loss.

Referring again to FIG. 2, focus control mechanism 17 allows a user to focus endoscope 10 by adjusting the distance between objective lens assembly 22 and CCD 24 by ±1 mm. As mentioned above, objective lens assembly 22 and CCD 24 are rigidly secured to inner tube 31 and CCD tube 32, respectively. The spacing between CCD 24 and lens assembly 22 is varied by moving CCD tube 32 axially along longitudinal axis 13 of endoscope 10. As will be discussed below, front face 25 of CCD 24 is moved by focus control mechanism 17 in response to rotation of focus ring 80 by the user.

Figure 4:
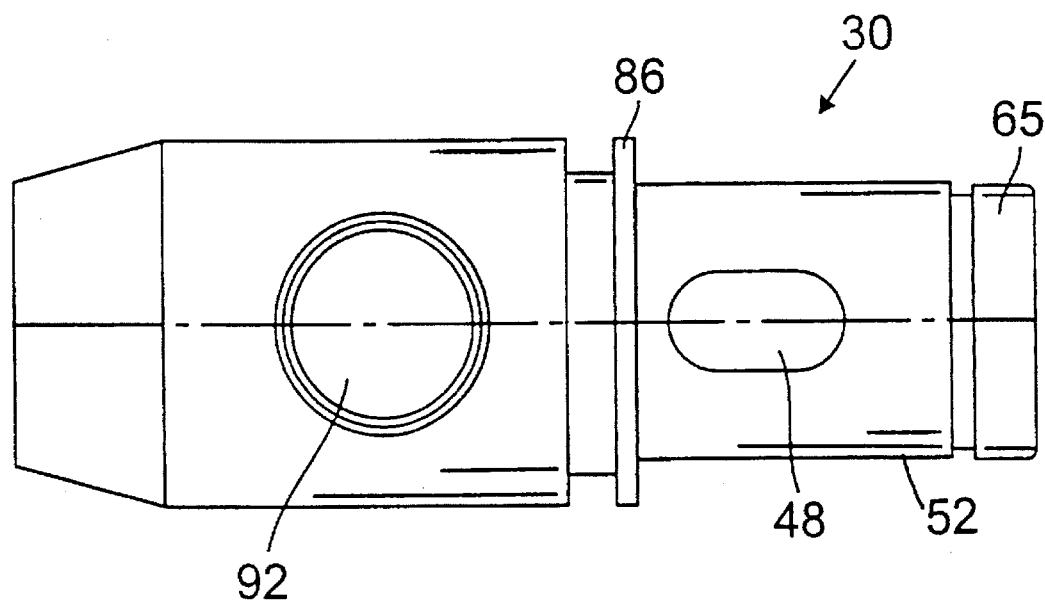
FIG. 4 is a top view of a main housing of the endoscope of FIG. 2.

Main housing 30 has a through hole 46 extending its length to receive CCD tube 32 and to allow cable 18 to pass through endoscope 10 (FIG. 4). A pair of oblong slots 48, 50 are disposed through opposite sidewalls of an end portion 65 of main housing 30 for respectively receiving a pair of cam screws 76, 78. Oblong slots 48, 50 have a length of about 0.35 inches, to provide the extent of forward and rearward motion of CCD tube 32 and are parallel to axis 13 for purposes to be described.

A cylindrical actuator 62 is interposed between main housing 30 and CCD tube 32 and is threaded to receive the proximal end of CCD tube 32. A pair of threaded holes 66, 67 orthogonal to axis 13 are disposed through the walls of actuator 62 and are aligned with oblong slots 48, 50 of main housing 30. A lock nut 63 secures actuator 62 to the proximal end of CCD tube 32.

Figure 5:
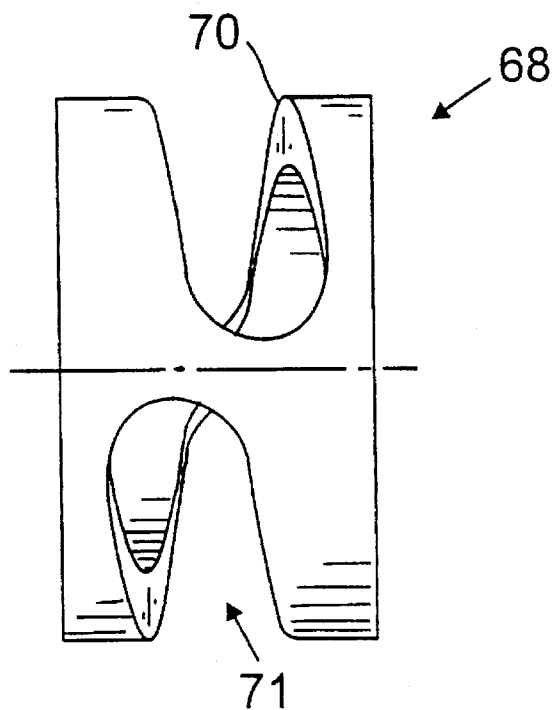
FIG. 5 is a side view of a focus sleeve of the endoscope of FIG. 2.

Along an outer surface of main housing 30 is a cylindrical focus sleeve 68 having a pair of diametrically opposed helical grooves 70, 71 each of which is aligned with a corresponding one of threaded holes 66, 67 of actuator 62 and a corresponding one of oblong slots 48, 50 (See FIG. 5). Each one of a pair of cam bearings 72, 74 having through holes 75, 77 engages a corresponding one of helical grooves 70, 71 and contacts actuator 62 along diametrically opposite helical surfaces of slots 70, 71. Each helical groove 70, 71 travels approximately 135° around focus sleeve 68 and has a width slightly larger than the diameter of cam bearings 72, 74. Cam bearings 72, 74 are made from a polymer plastic such as Delrin®, a product of Dupont Co., Wilmington, Del. Cam screws 76, 78 are placed within cam bearings 72, 74 and are screwed into threaded holes 66, 67 of actuator 62.

A focus ring 80 surrounds main housing 30 and is secured to focus sleeve 68 using a horizontally disposed pin 82 that engages a hole 85 of focus sleeve 68 (FIG. 2A). An 0-ring seal 98 is placed between main housing 30 and focus ring 80. Main housing 30 has a band 86 disposed on its outer surface that is proximal to the edge of slots 48, 50 nearest insertion section 12. Band 86 provides a support surface 88 for a thrust plate washer 90 placed between focus sleeve 68 and main housing 30.

A rear housing 102 is threaded onto a rear portion of main housing 30 with strain relief retainer 104. Retainer 104 holds strain relief 105 of cable 18. A second seal 100 (a Quad Ring, Gallagher No. AS568-014-559N) is positioned between main housing 30 and rear housing 102. Seals 98, 100 protect the inner workings of focus control mechanism 17 from the environment during surgical use and during sterilization.

Main housing 30 has an opening 92 along a side portion for receiving a light post 94. Light post 94 is a coupling member having a threaded end disposed in opening 92 with its opposite end having a fitting 96 for receiving a cable having fiber optic elements 26. The cable 18 is connected to a light source 110 (FIG. 6).

The mechanical configuration described provides a focus control mechanism 17 that is easily assembled and disassembled. For example, to disassemble focus control mechanism 17, rear housing 102 is unscrewed from the rear portion of main housing 30 and with retainer 104 is drawn along cable 18. Focus ring 80 axially separated from focus sleeve 68 by applying a sufficient force proximally along the length of handle 16 sufficient to separate pin 82 from hole 85 of focus sleeve 68. With focus ring 80 removed, cam screws 76, 78 are exposed and can be unscrewed from actuator 62 allowing cam bearings 72, 74 to be removed from through holes 75, 77 of focus sleeve 68. With cam bearings 72, 74 removed, focus sleeve 68 can be slid off of the end of main housing 30.

Referring to FIG. 6, endoscope 10, operating as a laparoscope, is shown inserted into a patient's abdomen 103 with a visual image 104 of the surgical site being transmitted to a video processor (i.e., camera control unit) 106 for viewing on a CRT display 108. A user focuses endoscope 10 by turning focus ring 80 in a circumferential clockwise or counterclockwise direction. With pin 82 firmly engaged within hole 85, focus sleeve 68 is mechanically bound to focus ring 80 such that any rotation of ring 80 is transferred to focus sleeve 68. Likewise, the transferred motion of the focus sleeve is conveyed to CCD tube 32 through cam screws 76, 78 and cam bearings 72, 74 causing CCD tube 32 to move linearly along axis 13 to change the spacing between lens assembly 22 and front face 25 of CCD 24, thereby focusing image 104. The helical path provided by grooves 70, 71 would normally cause CCD tube 32 and attached CCD 24 to rotate about axis 13, thus causing the image 104 being viewed on CRT 108 to also rotate. However, cam bearings 72, 74 are also captured within oblong slots 48, 50 of main housing 30 which are parallel with axis 13 so that CCD tube 32 is precluded from rotating and maintains an upright image on CRT 108 as CCD tube 32 is moved with respect to lens assembly 22.

Figure 7:
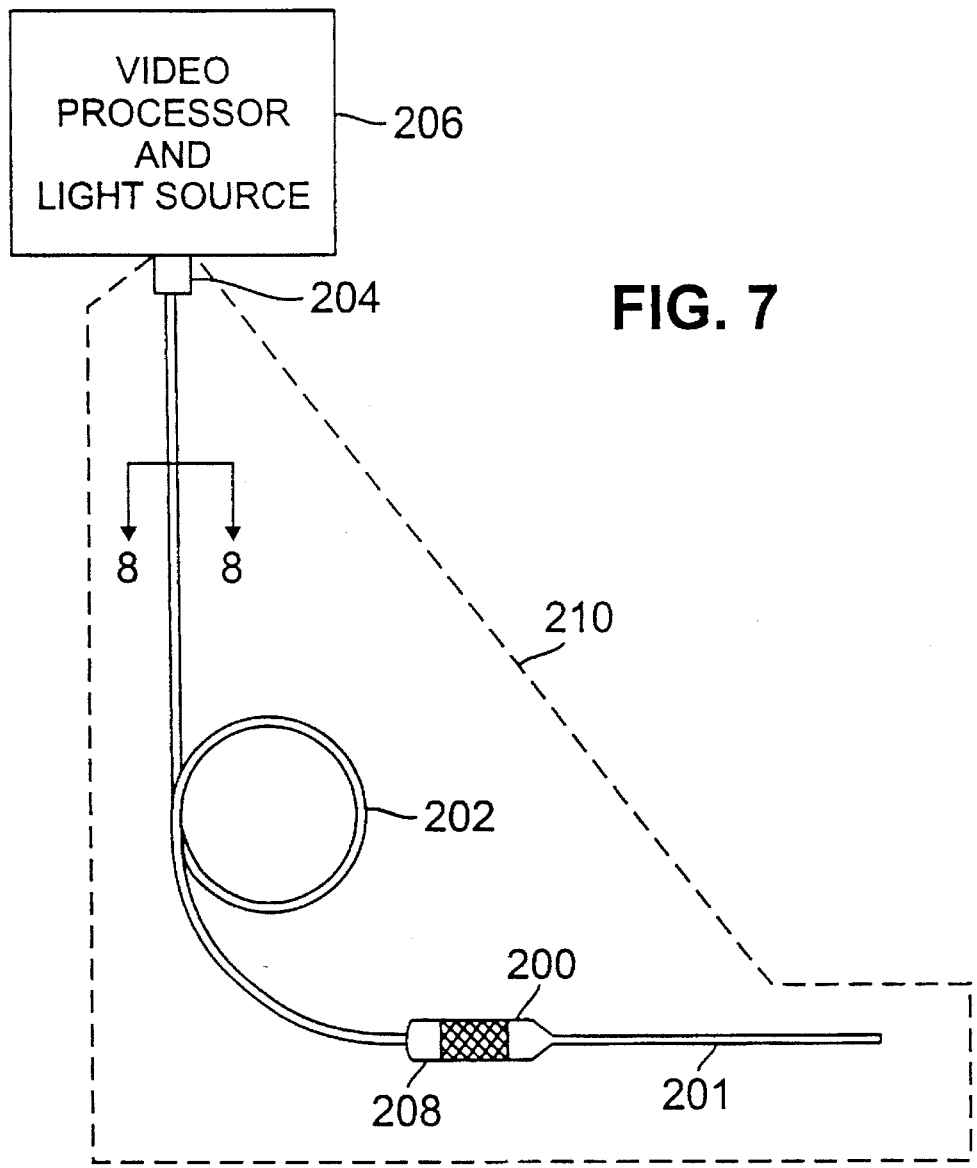
FIG. 7 is a diagrammatic view of an alternate embodiment of a disposable endoscope.

Other embodiments are within the scope of the claims. For example, referring to FIG. 7, a disposable electronic endoscope 200 is shown to include a sterilized elongated insertion section 201 and an integral sterilized cable 202 for providing both electrical power to a CCD sensor and light to fiber optic elements. In this embodiment, sterilized cable 202 has a connector 204 for connection to video processor and light source 206 (camera control unit) with the other end inserted directly into the rear axial portion 208 of endoscope 200. The attachment between cable 202 and disposable endoscope 200 is connector-less, with both electrical wiring and fiber optic elements being provided directly to an electro-optic module (CCD) and illumination area, respectively.

Figure 8:
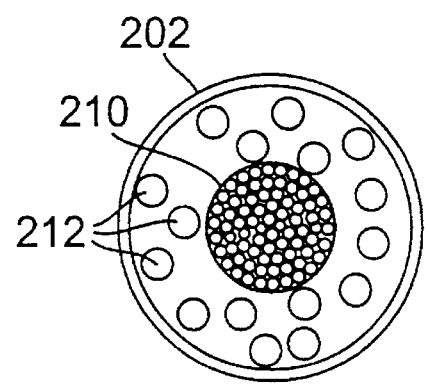
FIG. 8 is a cross-section of a portion of the disposable endoscope taken along lines 8—8 of FIG. 7.

In this embodiment, disposable endoscope 200 including sterilized cable 202 and connector 204 is provided in a sterile container 210 (as indicated by dashed lines). Container 210 maintains endoscope 200 in sterile storage until container 210 is opened at the time of use. When the endoscope procedure is completed, endoscope 200 is discarded. Alternatively, the endoscope 200 may be recycled by re-sterilizing and reenclosing endoscope 200 within a new sterile container. Sterilization procedures are described in U.S. Pat. No. 5,010,876 entitled "Arthroscopic Surgical Practice", assigned to the present assignee, which is hereby incorporated by reference. As shown in FIG. 8, cable 202 includes a fiber optic bundle 210 disposed in a center region of the cable 202 with electrical wires 212 for the electro-optic module surrounding fiber optic bundle 210.

Figure 9:
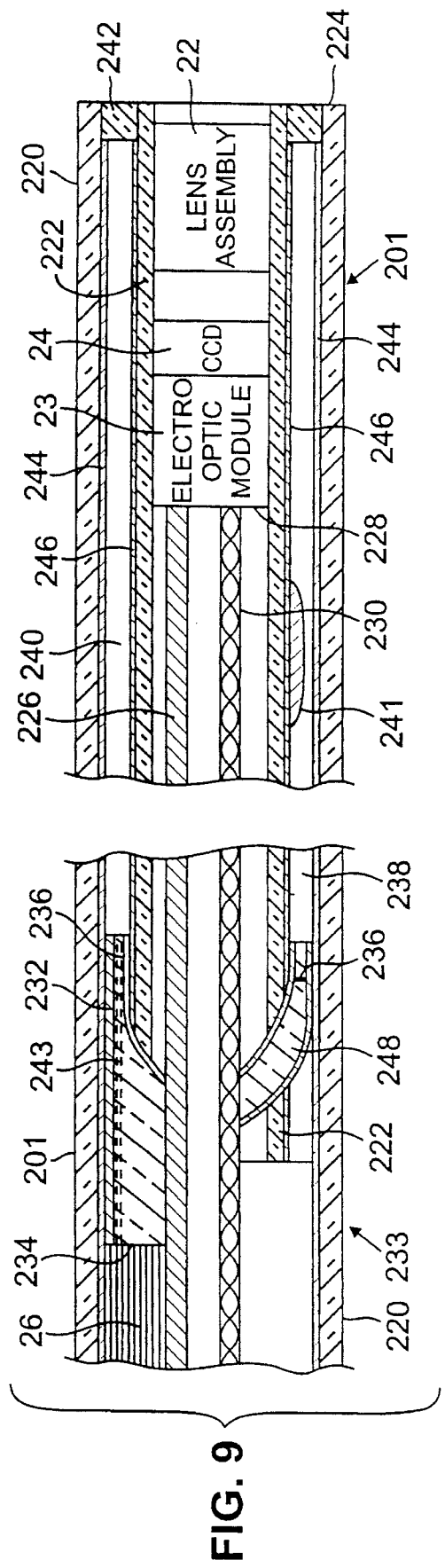
FIG. 9 is a cross-sectional side view of a distal region of another embodiment of a disposable endoscope.

Referring to FIG. 9, disposable endoscope 200 is shown having an alternative arrangement for providing illumination to surgical site 103 (FIG. 6). As was the case with endoscope 10 of FIG. 1, a sterilized elongated insertion section 201 of disposable endoscope 200 includes an outer tube 220 and a coaxially disposed inner tube 222. Inner tube 222 has objective lens assembly 22 rigidly mounted to a distal end 224 with an epoxy and electro-optic module 23 having a CCD 24 which is movable along the length of inner tube 222 with respect to lens assembly 22. (Lens assembly 22 may be made from plastic lens elements or lens elements that are hybrids of plastic and glass to reduce cost.) Electro-optic module 23 has a rod 226 attached to a rear portion 228 of module 23 which represents a mechanical coupling extending to focus control mechanism 17 (FIG. 2) at the proximal end of endoscope 200. A cable 230 is also connected to rear portion 228 of electro-optic module 23 to provide power and to receive electrical image signals.

Inner tube 222 terminates at a proximal end 233 of insertion section 201, where a molded plastic light connector 232 has a proximal end surface 234 coupled to fiber optic elements 26. Light connector 232 is formed in a manner such that connector 232 wraps and surrounds rod 226 and cable 230 in order to provide a light emitting end ring surface 236. End ring surface 236 is disposed within a cylindrical region 238 between outer tube 220 and inner tube 222. Light emitted from end ring surface 236 of connector 232 is propagated to distal end 224 through cylindrical region 238 of insertion section 201, via a glycerine 240, acting as a liquid light guide. A plastic lens ring 242 seals glycerine 240 within cylindrical region 238 at distal end 224 and projects the transmitted light to the image area. A thin metal membrane 241 is disposed within cylindrical region 238 along an outer surface of inner tube 222 to compensate for expansion and contraction of the volume of glycerine 240 due to temperature variations. Glycerine 240 is injected within cylindrical region 238 through a hole 243 provided from a proximal end 234 of connector 232 to a region along the periphery of end ring surface 236 of connector 232.

In this embodiment, outer tube 220 and inner tube 222 are fabricated from plastic to provide a relatively low cost and light weight disposable endoscope 200. Because tubes 220, 222 are made from plastic, reflective metal surfaces 244, 246 are plated onto an inner surface of outer tube 220 and an outer surface of inner tube 222. Reflective surfaces 244, 246 prevent light propagating through cylindrical region 238 from escaping through the walls of tubes 220, 222. Similarly, outer surfaces, (excepting end ring surface 236 of light connector 232), are plated with a reflective layer 248.

Figure 10:
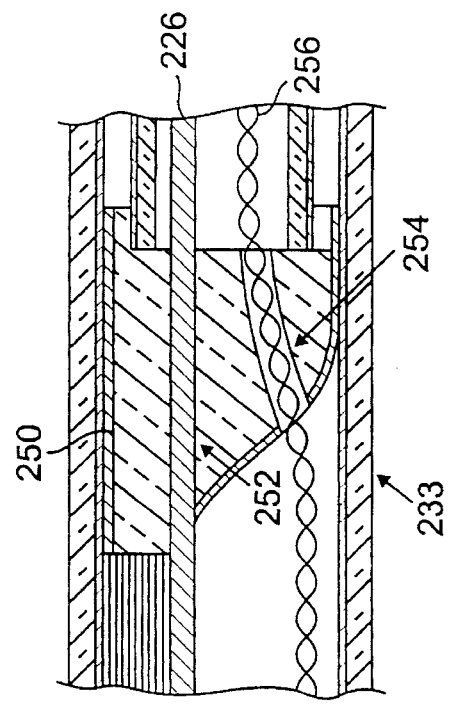
FIG. 10 is a cross-sectional side view of a portion of the distal region of another embodiment of a disposable endoscope.

Referring to FIG. 10, an alternative light connector 250 is shown disposed at proximal end 233 of insertion section 201. Light connector 250 has a pair of holes 252, 254 to permit rod 226 and wires 256, respectively to pass through connector 250 and connect to electro-optic module 228 in the same manner shown in FIG. 9.

As shown in FIG. 11, in another embodiment, an electronic endoscope 300 includes a solid state image sensor 302 (e.g. a charge-coupled device (CCD)) disposed at a proximal end 304 of endoscope 300. A fiber optic bundle 306 extends from proximal end 304 of endoscope 300 through an insertable portion 308 to a region adjacent to lens assembly 310. Fiber optic bundle 306 and CCD 302 are each coupled to independent focus control mechanisms 312 and 314, respectively. In operation, fiber optic control focus mechanism 312 is adjusted to move fibre optic bundle 306 axially with respect to lens assembly 310, thereby focusing the image of object 316 onto the distal end 318 of the optical fibers 306. The image is conveyed to the proximal end 320 of fiber optic bundle 306 for conversion to an electrical signal by CCD 302. The image at proximal end 320 is focused onto CCD 302 with camera focus control mechanism 314 to provide a clear image to a front face 322 of CCD 302.

In another embodiment, first cylindrical member 33 and second extension member 34 (FIGS. 1 and 2) of CCD tube 32 can be formed as a single continuous tube.

In another alternative embodiment, focus ring 80 is coupled to CCD tube 32 magnetically rather than mechanically. One example of such a magnetic coupling technique is described in U.S. Pat. No. 5,056,902, entitled "Magnetically Coupled Actuator", assigned to the present assignee, and incorporated herein by reference. According to this technique, focus ring 80 includes an element (such as a magnet) that is ferromagnetically coupled to actuator 62 through the external wall of housing 30. (Alternatively, the magnet can be disposed on actuator 62.)

In another embodiment, disposable endoscope 200 includes a plastic light transmission element substituted for glycerine 240 in cylindrical region 238 to propagate externally provided light to distal end 224 of insertion section 201. The plastic light transmission element may be a single piece and may incorporate both molded plastic light connector 232 and plastic lens ring 242.

What is claimed is:

1. An endoscope apparatus for internal inspection of an object, comprising an insertion section elongated along a longitudinal axis between distal end to be inserted into said object and a proximal end to be manipulated by a user, said distal end enclosing a chamber, a lens assembly disposed in said chamber, an electro-optical sensor mounted in said chamber proximally of said lens assembly said sensor being movable along the longitudinal axis, and a focusing mechanism having a rotatable manipulator at said proximal end and a mechanical coupling connecting said rotatable manipulator to said sensor for causing said sensor to move along the longitudinal axis for focusing in response to rotation of said rotatable manipulator, said rotatable manipulator having a surface transverse to the longitudinal axis, said transverse surface being disposed in opposing face-to-face engagement with a transverse surface of said mechanical coupling, said rotatable manipulator being connected to said mechanical coupling at said transverse surfaces by a coupling oriented generally parallel to the longitudinal axis so that said manipulator can be disconnected from said mechanical coupling by moving said rotatable manipulator axially away from said mechanical coupling along said longitudinal axis.

2. The apparatus of claim 1 wherein said mechanical coupling comprises a rigid actuator coupled between said rotatable manipulator and said sensor, said actuator moving along the longitudinal axis in response to rotation of said rotatable manipulator.

3. The apparatus of claim 2 wherein said mechanical coupling further comprises a helical surface, and said rigid actuator includes a follower configured to engage said helical surface and to move along said helical surface in response to rotation of said rotatable manipulator.

4. The apparatus of claim 3 wherein said helical surface is disposed on a member connected to said rotatable manipulator by said coupling.

5. The apparatus of claim 3 wherein said follower comprises a projection on said rigid actuator, said helical surface comprises a groove on said rotatable manipulator, said follower riding within said groove, and said mechanical coupling further comprises a slot provided along a portion of the length of said insertion section, said follower riding within said slot.

6. The apparatus of claim 5 wherein said slot is disposed parallel to said longitudinal axis, engagement of said follower and said slot avoiding rotation of said electro-optical sensor during said focusing.

7. The apparatus of claim 2 wherein said rotatable manipulator comprises a sleeve surrounding and rotatable around an external wall of said proximal end.

8. The apparatus of claim 2 wherein said manipulator is rotatable around an external wall of said proximal end and includes an element that is ferromagnetically coupled to said rigid actuator through said wall.

9. The endoscope apparatus of claim 1 further comprising an optical fiber for carrying light along the length of said insertion section to an illumination outlet at said distal end.

10. The endoscope apparatus of claim 9 further comprising an electrical cable for carrying electrical signals from said sensor along the length of said insertion section to said proximal end, and a flexible conduit connecting said proximal end to a control unit, said electrical cable and said optical fiber carried within said flexible conduit.

11. The endoscope apparatus of claim 10 wherein said flexible conduit has a central axis collinear with said longitudinal axis.

12. An endoscope apparatus for internal inspection of an object, comprising an insertion section elongated along a longitudinal axis between a distal end to be inserted into said object and a proximal end to be manipulated by a user, said distal end enclosing a chamber, a lens assembly disposed in said chamber, an electro-optical sensor mounted in said chamber proximally of said lens assembly, said sensor being movable along the longitudinal axis, a focusing mechanism having a focus control element at said proximal end and a mechanical coupling connecting said focus control element to said sensor for causing said sensor to move along said longitudinal axis for focusing in response to activation of said focus control element, said focus control element including a manipulator that is accessible to and rotatable by said user to provide said activation, said manipulator including an outer sleeve having a surface transverse to said longitudinal axis, said mechanical coupling comprising a helical surface disposed on an inner sleeve which surrounds and is rotatable around said proximal end, said outer sleeve surrounding said inner sleeve with said transverse surface of said outer sleeve being disposed in opposing, face-to-face engagement with a transverse surface of said inner sleeve, said inner sleeve and said outer sleeve being connected at said transverse surfaces by a coupling oriented generally parallel to said longitudinal axis so that said outer sleeve can be disconnected from said inner sleeve by moving said outer sleeve axially away from said inner sleeve along the longitudinal axis, and a rigid actuator including a follower configured to engage said helical surface and to move along said helical surface in response to rotation of said rotatable manipulator, thereby to cause said rigid actuator to move along the longitudinal axis and move said sensor with respect to said lens assembly.

13. The apparatus of claim 12 wherein said coupling includes a pin for joining said inner and outer sleeves.

14. An endoscope apparatus for internal inspection of a object, comprising an insertion section elongated along a longitudinal axis between a distal end to be inserted into said object and a proximal end to be manipulated by a user, said distal end enclosing a chamber, a lens assembly disposed in a chamber in said distal end, an electro-optical sensor mounted in said chamber proximally of said lens assembly, said sensor being movable along said longitudinal axis, and a focusing mechanism having a rotatable focus manipulator at said proximal end, having a surface transverse to said longitudinal axis and a mechanical coupling having a transverse surface disposed in opposing face-to-face engagement with said transverse surface of said manipulator, said manipulator being connected to said mechanical coupling at said transverse surfaces by a coupling oriented generally parallel to the longitudinal axis so that said manipulator can be disconnected from said mechanical coupling by moving said manipulator axially away from said mechanical coupling along said longitudinal axis, said mechanical coupling having a helical surface disposed on a member connected to said manipulator by a coupling, and a rigid actuator having a follower configured to engage and move along said helical surface and to cause said actuator to move along said longitudinal axis in response to rotation of said manipulator.

15. An endoscope apparatus for internal inspection of an object, comprising an insertion section elongated along a longitudinal axis between a distal end to be inserted into said object and a proximal end to be manipulated by a user, a lens assembly disposed in a chamber in said distal end, an image transmitting device mounted in said chamber of said distal end, said image transmitting device being movable along said longitudinal axis, and a focusing mechanism having a rotatable manipulator at said proximal end and a mechanical coupling connecting said rotatable manipulator to said image transmitting device for causing said image transmitting device to move along said longitudinal axis with respect to said lens assembly for focusing in response to rotation of said rotatable manipulator, said rotatable manipulator having a surface transverse to the longitudinal axis, said transverse surface being disposed in opposing face-to-face engagement with a transverse surface of said mechanical coupling, said rotatable manipulator being connected to said mechanical coupling at said transverse surfaces by a coupling oriented generally parallel to the longitudinal axis so that said manipulator can be disconnected from said mechanical coupling by moving said rotatable manipulator axially away from said mechanical coupling along said longitudinal axis.

16. The apparatus of claim 15 wherein said image transmitting device includes an electro-optical sensor for converting said image into an electrical signal.

* * * * *

UNITED STATES PATENT AND TRADEMARK OFFICE
CERTIFICATE OF CORRECTION

PATENT NO.   : 5,575,757

DATED        : November 19, 1996

INVENTOR(S)  : John E. Kennedy et al.

It is certified that error appears in the above-identified patent and that said Letters Patent is hereby corrected as shown below:

On the cover sheet, in the "References Cited", "U.S. Patent Documents" section, add:

4,574,783    03/1986    Kazuhiro et al.
4,730,729    03/1988    Monch

Col. 5, line 21, replace "0-ring" with --O-ring--;

Col. 8, claim 1, line 5, after "between" insert --a--;

Col. 10, claim 14, line 10, after "manipulator" insert --,--.

Signed and Sealed this

Eighth Day of July, 1997

Attest:

BRUCE LEHMAN

Attesting Officer

Commissioner of Patents and Trademarks